(12) United States Patent
Saute et al.

(10) Patent No.: US 8,192,729 B2
(45) Date of Patent: Jun. 5, 2012

(54) COMPOSITION AND METHOD FOR HAIR STRAIGHTENING

(76) Inventors: Robert Saute, Los Angeles, CA (US); Steve Saute, La Canada Flintridge, CA (US)

(*) Notice: Subject to any disclaimer, the term of this patent is extended or adjusted under 35 U.S.C. 154(b) by 0 days.

(21) Appl. No.: 12/655,209

(22) Filed: Dec. 21, 2009

(65) Prior Publication Data

US 2011/0146699 A1    Jun. 23, 2011

(51) Int. Cl.
*A61Q 5/04* (2006.01)
(52) U.S. Cl. .................................. 424/70.2; 424/70.12
(58) Field of Classification Search .................. None
See application file for complete search history.

(56) References Cited

U.S. PATENT DOCUMENTS

| | | | | |
|---|---|---|---|---|
| 5,165,427 A | * | 11/1992 | Borish | 132/204 |
| 5,294,230 A | * | 3/1994 | Wu et al. | 8/127.51 |
| 5,681,554 A | * | 10/1997 | Cannell et al. | 424/70.14 |
| 6,238,658 B1 | | 5/2001 | Nguyen et al. | |
| 6,306,377 B1 | * | 10/2001 | Coppola et al. | 424/70.1 |
| 6,537,564 B1 | * | 3/2003 | Mabratu | 424/401 |
| 6,602,493 B2 | * | 8/2003 | Akhter et al. | 424/70.1 |
| 6,861,077 B1 | | 3/2005 | Cannell et al. | |
| 2005/0136016 A1 | * | 6/2005 | Malle et al. | 424/70.2 |
| 2005/0186232 A1 | | 8/2005 | Malle et al. | |
| 2006/0104928 A1 | * | 5/2006 | Furtado | 424/70.2 |
| 2006/0222613 A1 | * | 10/2006 | Teramoto | 424/70.5 |

FOREIGN PATENT DOCUMENTS

| WO | WO99/26591 | * | 6/1999 |
|---|---|---|---|
| WO | WO2007/032762 | * | 3/2007 |

OTHER PUBLICATIONS

Flick, E.W., Cosmetic Additives—An Industrial Guide, 1991, William Andrew Publishing/Noyes.*
International Nomenclature of Cosmetic Ingredients.*

* cited by examiner

*Primary Examiner* — Jyothsna Venkat
(74) *Attorney, Agent, or Firm* — Sandy Lipkin

(57) ABSTRACT

A composition and method of use therefor that allows for permanent straightening or curl of human hair that is not irritating to the skin, that does not have an obnoxious odor, that is significantly less damaging to hair, that allows for the immediate shampooing of hair thereafter and that provides for re-treatment of the hair without additional damage, primarily using urea and high temperatures to break and reform disulfide bonds as a means to allow for the penetration of low molecular weight proteins into the shaft of the hair.

2 Claims, No Drawings

COMPOSITION AND METHOD FOR HAIR STRAIGHTENING

REFERENCE TO PRIOR APPLICATION

This application claims the priority of PCT application PCT/US2007/014612, filed Jun. 30, 2007 entitled COMPOSITION AND METHOD FOR HAIR STRAIGHTENING by Robert Saute and Steven Saute.

BACKGROUND OF THE INVENTION

1. Field of the Invention

The present invention relates generally to the field of the hair manipulation products and systems, and particularly to a process and series of compounds that permanently straighten and/or curl hair.

2. Description of the Prior Art

The art of curling hair dates back as far as ancient Egypt, when the "mud method" was used. Wooden sticks used in the "mud method" were later replaced by metal rods, and as time progressed the rods were heated during the process. This use of heating rods was the foundation for the use of curling tongs that were still popular in the 1930s. The first permanent waving method introduced into the United States originated in France in 1884. This method included the use of concentrated seawater and heat.

All previous methods were abandoned when Charles Nessler devised a process for softening the hair using borax in 1906. Evans and McDonough introduced a method using mercaptans, first as depilatories and as cold-waving agents. The substituted mercaptans were found preferable in curling the hair because they are more efficient and have a less objectionable odor.

Various modifications to the use of the mercaptans products have been developed to improve the curling power and to reduce the damage done to the hair during the curling process. The most popular waving preparations have an alkaline pH in the range of 8.0 to 9.0. Acid waves, using derivatives of thioglycolic acid are simple amide salts and esters. Amides and esters of thioglycolic acid are potential sensitizers. These products are of little commercial importance due to their instability and irritation potential. Sulfite containing products can be used in tepid waving and found use in hair straightening in the presence of large amounts of urea and isopropyl alcohol.

Tepid waving, a form of heat waving has been used to increase reaction time between sulfites and hair. The temperatures used are moderate and well tolerated by consumers under a hair dryer. Steam flat irons and dry flat irons are used to straighten hair. When the tepid method is used the strength of conventional heat waving preparation is increased, while it is decreased in the cold wave products. Temperatures in the range of 20° C. to as high as 80° C. have been used in these procedures.

The physical process of permanently waving or straightening hair is caused by a change in the molecular configuration of the keratin molecule, giving the hair a lasting curl that cannot be changed by physical means. This change in configuration can be accomplished by the use of high temperatures, or by chemicals such as alkalis and certain sulfur compounds adjusted to a proper pH, in bases having a dissociation constant of less than $5 \times 10^{-3.5}$. Water curls and temporary sets differ from permanent waves in that the curls are formed when unstable cross linkages are present, and tend to return to their normal configuration when moistened. The hair in its normal state is made up of regularly folded polypeptide chains with cystine, hydrogen and polar or salt linkages.

In order to permanently curl or straighten the hair, one must break the disulfide bonds. Before the chemical can break these disulfide bonds it must penetrate the cuticle of the hair. Both permanent waving of the hair and straightening of the hair have been popular ways of modifying hairstyles. People with unmanageable tight curly hair frequently have their hair straightened. Straightening the hair has been accomplished by using highly viscous alkaline preparations; the high viscosity helps to keep the preparation off the scalp. The most popular preparations are formulated with sodium hydroxide or potassium hydroxide. The pHs of these preparations range from eight to twelve.

All prior art products either permanently straighten or curl the hair using ingredients that are irritating to the skin. Consequently, manufacturers caution people who use these products to use protective gloves to apply the creams or solutions to the hair. They recommend protecting the skin of the person receiving the straightening or curling service as much as possible.

In general the alkaline products are left on the hair for a specified length of time. A test curl is taken to determine if the time of contact is sufficient to produce a satisfactory curl. When straightening the hair, the product is placed on the hair and stretched using a styling tool or brush. Large curlers are used to obtain wavy hair. In both curling and straightening processes, there is a second step required to reform the disulfide bonds in the hair. This is necessary to make reconfiguration permanent.

The shortcomings in the prior art are many fold. The primary drawback is the potential damage to the skin of the person receiving the treatment based on the high pH of the solutions used. Additionally, the processes provide a noxious smell that takes days or weeks to leave the hair. Also, universally, the hair is left in a damaged state and weaker than prior to the treatment. Accordingly, when the treated hair grows out, in order to maintain the curl or straightened state of the hair, only the newly grown hair can be treated without further damaging the hair. Another drawback to prior art methods is that the hair cannot be shampooed for several days after the procedure because the achieved result will be negated by shampooing in the days following.

It is the object of the present invention to overcome all of the drawbacks of the prior art by providing a composition of products and a process for use thereof that achieves the desired ends without any of the stated drawbacks.

It is an object of the invention to provide a product and process for straightening or curling hair that does not damage the skin of the person receiving the treatment based on the high pH of the solutions used.

It is an object of the invention to provide a product and process for straightening or curling hair that does not leave a noxious smell in the hair of the person.

It is an object of the invention to provide a product and process for straightening or curling hair that does not leave the hair in a damaged state and that actually may leave the hair in better shape than prior to the treatment.

It is an object of the invention to provide a product and process for straightening or curling hair that does not incur damage with multiple treatments.

It is an object of the invention to provide a product and process for straightening or curling hair that does not become undermined by the immediate shampooing of the hair after treatment.

SUMMARY OF THE INVENTION

The preferred embodiment of the present invention teaches a kit for the straightening or curling of hair, comprising a first solution further comprising 75-80% water, 4-6% PEG-12, 2-5% hydrolyzed corn protein, 2-5% hydrolyzed soy protein, 2-8% urea, 0.5-2.5% polysorbate 20, 0.10-0.20% methylparaben, 0.02-0.06% propylparaben, and 0.5-1.5% phenoxyethanol; a second solution further comprising 74-77% water, 3-7% stearylkonium chloride, 2-5% glyceryl stearate and PEG 100 stearate, 1.5-3.5% cetyl alcohol, 0.5-1.5% stearyl alcohol, 0.5-1.5% theobroma cacao seed butter, 0.3-0.7% dimethoconol meadowfomate, 0.5-1.5% paraffinum liquidum, 0.5-2.5% sodium chloride PCA, 1-3% glycerin, 0.5-2.5% urea, 0.02-0.06% tetra sodium EDTA, 0.1-0.5% citric acid, 0.3-0.7% panthanol, 0.5-2.5% hydrolyzed corn protein, 0.5-1.5% hydrolyzed oat protein, 0.3-0.7% hydrolyzed soy protein, 0.5-1.5% sorbic acid, and 0.1-0.3% methylisothiazolinone; and a third solution further comprising 82-86% water, 2-4% cetrimonium bromide, 0.5-2.5% glyceryl stearate and PEG 100 stearate, 1.5-3.5% cetyl alcohol, 1.5-3.5% stearyl alcohol, 0.5-1.5% glycerin, 0.3-0.7% tritcum vulgare (wheat) germ oil, 0.5-1.5% hydrolyzed corn protein, 0.3-0.7% hydrolyzed wool protein, 0.1-0.3% hydrolyzed collagen protein, 0.5-1.5% citric acid, 0.01-0.05% disodium EDTA, 0.03-0.07% methylisothiazzolinone, and 0.05-1.5% sorbic acid.

The above embodiment can be further modified by defining that the first solution further comprises 3-7% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by defining that the first solution further comprises 0.5-1.5% fragrance.

The above embodiment can be further modified by defining that the second solution further comprises 1.5-3.5% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by defining that the second solution further comprises 0.1-0.3% fragrance.

The above embodiment can be further modified by defining that the third solution further comprises 1-3% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by defining that the third solution further comprises 0.1-0.3% fragrance.

The above embodiment can be further modified by defining that the third solution further comprises 0.1-0.3% PABA.

A second embodiment of the instant invention teaches a method for straightening or curling hair comprising the steps of shampooing the hair; drying the hair thoroughly; shaking a bottle of a first solution to remove and dissolve any precipitates, said first solution further comprising 75-80% water, 4-6% PEG-12, 2-5% hydrolyzed corn protein, 2-5% hydrolyzed soy protein, 2-8% urea, 0.5-2.5% polysorbate 20, 0.10-0.20% methylparaben, 0.02-0.06% propylparaben, and 0.5-1.5% phenoxyethanol; spraying said first solution on the hair; providing sufficient time for said first solution to soak into the hair; applying to the hair soaked with said first solution a hot iron set a temperature between 400 and 450 degrees Fahrenheit; with said hot iron, straighten the hair using tension and a comb between five and ten times as dictated by the type of hair; spraying a second solution on the hair, said second solution further comprising 74-77% water, 3-7% stearylkonium chloride, 2-5% glyceryl stearate and PEG 100 stearate, 1.5-3.5% cetyl alcohol, 0.5-1.5% stearyl alcohol, 0.5-1.5% theobroma cacao seed butter, 0.3-0.7% dimethoconol meadowfomate, 0.5-1.5% paraffinum liquidum, 0.5-2.5% sodium chloride, 1-3% glycerin, 0.5-2.5% urea, 0.02-0.06% tetra sodium EDTA, 0.1-0.5% citric acid, 0.3-0.7% panthanol, 0.5-2.5% hydrolyzed corn protein, 0.5-1.5% hydrolyzed oat protein, 0.3-0.7% hydrolyzed soy protein, 0.5-1.5% sorbic acid, and 0.1-0.3% methylisothiazolinone; straighten the hair four times with a flat iron with a comb and tension, said flat iron set at a temperature between 400 and 450 degrees Fahrenheit; spray on the hair a third solution, said third solution further comprising 82-86% water, 2-4% cetrimonium bromide, 0.5-2.5% glyceryl stearate and PEG 100 stearate, 1.5-3.5% cetyl alcohol, 1.5-3.5% stearyl alcohol, 0.5-1.5% glycerin, 0.3-0.7% tritcum vulgare (wheat) germ oil, 0.5-1.5% hydrolyzed corn protein, 0.3-0.7% hydrolyzed wool protein, 0.1-0.3% hydrolyzed collagen protein, 0.5-1.5% citric acid, 0.01-0.05% disodium EDTA, 0.03-0.07% methylisothiazolinone, and 0.05-1.5% sorbic acid; straighten the hair four times with a flat iron with a comb and tension, said flat iron set at a temperature between 400 and 450 degrees Fahrenheit; let hair cool for 30 minutes; rinse with water; apply said third solution; rinse with water; and style as desired.

The above embodiment can be further modified by defining that the first solution further comprises 3-7% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by defining that the first solution further comprises 0.5-1.5% fragrance.

The above embodiment can be further modified by defining that the second solution further comprises 1.5-3.5% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by further defining that the second solution further comprises 0.1-0.3% fragrance.

The above embodiment can be further modified by further defining that the third solution further comprises 1-3% extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia).

The above embodiment can be further modified by defining that the third solution further comprises 0.1-0.3% fragrance.

The above embodiment can be further modified by defining that the third solution further comprises 0.1-0.3% PABA.

DETAILED DESCRIPTION OF A PREFERRED EMBODIMENT

The instant invention seeks to provide a new hair straightening and curling process and product that produces permanent reconfiguration of hair. Three unique products are applied to the hair and heated with a dry or steam iron according to specific instructions. The hair can be shampooed immediately after the procedure, leaving a permanently curled or straightened hair in excellent condition. The treatment does not leave an obnoxious odor in the hair or release obnoxious odors while the hair is being treated. A complete process can be accomplished in less than half the time it takes to accomplish the task with prior art processes and products.

There are three compositions used in the process described herein. The three products used in the process of rearranging the molecular structure of the hair to create either curly or straight hair are unique in that they are not alkaline and do not produce obnoxious odors. These products are not considered irritants or sensitizers. The application of these products does not require the use of rubber gloves.

Composition of Product 1

The first product consists of several hydrolyzed proteins derived from land and sea. These hydrolyzed proteins consist of amino acids, peptides and polypeptides. The first product also consists of humectants, such as glycerin, sodium salt PCA and urea; surfactants, such as those that are ionic and nonionic, sodium lauryl sulfate and polysorbate; lubricants, such as PEG-12, propylene glycol and butylenes glycol; fragrances, herbal extracts and preservatives.

Product one can be made in one vessel by one skilled in the art of compounding, while controlling the stirring so as to avoid the entrapment of air therein.

| Formulation Example for Product 1 | |
| --- | --- |
| Ingredient | % by weight |
| Water | 77.21 |
| PEG-12 | 5.0 |
| Extracts of *Gingko Biloba*, Matricaria (*Chamomilla Recuite*), Orange Peel (*Citrus Aurantium Dulcis*), *Althea Officinalis*, Yarrow (*Achillea Millefolium*), Fennel (*Foeniuculum Vulgare*), and Licorice (*Glycrrhiz Glabia*) | 5.0 |
| Hydrolyzed corn protein | 3.5 |
| Hydrolyzed soy protein | 3.5 |
| Urea | 3.0 |
| Polysorbate 20 | 1.5 |
| Methylparaben | 0.15 |
| Propylparaben | 0.04 |
| Phenoxyethanol | 1.0 |
| Fragrance | 0.1 |

Composition of Product 2

The second product consists of several hydrolyzed proteins derived from land and sea. These hydrolyzed proteins consist of amino acids, peptides and polypeptides. The second product also consists of humectants, such as glycerin, sorbitol, urea and the sodium salt PCA; surfactants, such as those that are ionic and nonionic, steareth 2, oleth 10, stearylkonium chloride, cetronium bromide; rheology modifiers, such as fatty alcohols, synthetic and natural polymers; shine conditioners, such as natural butters, silicones, natural and synthetic oils; fragrances, herbal extracts and preservatives.

Product two can be made in one vessel by one skilled in the art of compounding, while controlling the stirring so as to avoid the entrapment of air therein. During compounding, product two should be heated to 75° C. before cooling.

| Formulation Example for Product 2 | |
| --- | --- |
| Ingredient | % by weight |
| Water | 76.26 |
| Stearylkonium Chloride | 5.0 |
| Glyceryl Stearate and PEG 100 Stearate | 3.0 |
| Extracts of *Gingko Biloba*, Matricaria (*Chamomilla Recuite*), Orange Peel (*Citrus Aurantium Dulcis*), *Althea Officinalis*, Yarrow (*Achillea Millefolium*), Fennel (*Foeniuculum Vulgare*), and Licorice (*Glycrrhiz Glabia*) | 2.5 |
| Cetyl Alcohol | 1.0 |
| Stearyl Alcohol | 0.5 |
| Theobroma Cacao Seed Butter | 1.0 |
| Dimethiconol Meadowfomate | 0.5 |
| Paraffinum Liquidum | 1.0 |
| Sodium salt PCA | 1.5 |
| Glycerin | 2.0 |
| Urea | 1.5 |
| Tetra Sodium EDTA | 0.04 |
| Citric Acid | 0.30 |
| Panthanol | 0.50 |
| Hydrolyzed Corn Protein | 1.5 |
| Hydrolyzed Oat Protein | 1.0 |
| Hydrolyzed Soy Protein | 0.50 |
| Sorbic Acid | 0.10 |
| Methylisothiazolinone | 0.10 |
| Fragrance | 0.20 |

Composition of Product 3

The third product consists of several hydrolyzed proteins derived from land and sea. These hydrolyzed proteins consist of amino acids, peptides and polypeptides. The third product also consists of humectants, such as glycerin, urea and panthenol; surfactants, such as those that are cationic and nonionic, stearomidopropyl dimethylamine and lipmulse 165; rheology modifiers, such as fatty alcohols, synthetic and natural and polymers; chelating agents, such as citric acid, sodium salt of ethlenediamine tetraacetic acid; shine and conditioning agents, such as natural and synthetic oils, butters and silicones; fragrances, herbal extracts and preservatives.

Product three can be made in one vessel by one skilled in the art of compounding, while controlling the stirring so as to avoid the entrapment of air therein. During compounding, product three should be heated to 75° C. before cooling.

| Formulation Example for Product 3 | |
| --- | --- |
| Ingredient | % by weight |
| Water | 84.57 |
| Cetrimonium Bromide | 3.0 |
| Glyceryl Stearate & PEG 100 Stearate | 1.5 |
| Cetyl Acohol | 2.5 |
| Stearyl Alcohol | 2.5 |
| Glycerin | 1.0 |
| *Trictum Vulgare* (Wheat) Germ Oil | 0.50 |
| Hydrolyzed Corn Protein | 1.0 |
| Hydrolyzed Wool Protein | 0.5 |
| Hydrolyzed Collagen Protein | 0.2 |
| PABA | 0.25 |
| Citric Acid | 0.1 |
| Disodium EDTA | 0.03 |
| Methylisothiazzolinone | 0.05 |
| Sorbic Acid | 0.1 |
| Extracts of *Gingko Biloba*, Matricaria (*Chamomilla Recuite*), Orange Peel (*Citrus Aurantium Dulcis*), *Althea Officinalis*, Yarrow (*Achillea Millefolium*), Fennel (*Foeniuculum Vulgare*), and Licorice (*Glycrrhiz Glabia*) | 2.0 |
| Fragrance | 0.2 |

Additional additives to each product may be used for obtaining particular effects such as volatile solvents, colors, sunscreens, etc.

Once compounded, these three products need to be used following a very specific procedure in order to achieve the desired result with the desired benefits over the prior art. The composition of these three products used in conjunction with the procedure defined herein provides excellent results in either straightening or curling the hair.

The procedure used to straighten the hair consists of shampooing the hair with a cleansing shampoo, then blow-drying the hair. Product one is applied to the hair and left on for a prescribed time.

The hair is then hot ironed while applying stress to the hair with a styling tool or brush. The ironing procedure is repeated several times while maintaining a suitable temperature with the iron.

The straightened hair is treated with product two for a suitable amount of time. The hot iron process is repeated as with product one.

After the process with product two, product three is applied and the hot iron treatment is repeated as with product one. After the process of applying the iron after applying product three, the hair can be rinsed or may be shampooed and dried. It is to be understood that one of ordinary skill in the art would be able to substitute the appropriate curling steps for the straightening steps when utilized to curl rather than straighten hair. The detailed process is outlined below.

Step One: Wash the hair with an appropriate shampoo for the hair type.

Step Two: Dry the hair thoroughly.

Step Three: Shake the product one bottle thoroughly to disperse any precipitate.

Step Four: Spray the product one on the hair.

Step Five: Let product one soak into the hair for at least five minutes. If the product dries before the next step, then reapply.

Step Six: Use a hot iron at a temperature of 420° F.

Step Seven: Straighten the hair with the iron at 420° F. using the tension and a comb.

Step Eight: Repeat at least five times, up to ten times or more, depending on the hair type.

Step Nine: Put the product two on the hair.

Step Ten: Straighten the hair with a flat iron at 420° F. with a comb for tension.

Step Eleven: Repeat three times.

Step Twelve: Put product three on the hair.

Step Thirteen: Straighten with a flat iron at 420° F. with a comb for tension.

Step Fourteen: Repeat three times.

Step Fifteen: Let hair cool for 30 minutes.

Step Sixteen: Rinse with water.

Step Seventeen: Apply product three and rinse again.

Step Eighteen: Style as desired.

The illustrations and examples provided herein are for explanatory purposes and are not intended to limit the scope of the appended claims. This disclosure is to be considered an exemplification of the principles of the invention and is not intended to limit the spirit and scope of the invention and/or claims of the embodiment illustrated. Those skilled in the art will make modifications to the invention for particular applications of the invention.

What is claimed is:

1. A kit for the straightening or curling of hair, comprising a first solution comprising 75-80% water, 4-6% PEG-12, 2-5% hydrolyzed corn protein, 2-5% hydrolyzed soy protein, 2-8% urea, 0.5-2.5% polysorbate 20, 0.10-0.20% methylparaben, 0.02-0.06% propylparaben, 0.5-1.5% phenoxyethanol 3-7% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia) and 0.5-1.5% fragrance;

a second solution comprising 74-77% water, 3-7% stearylkonium chloride, 2-5% glyceryl stearate and PEG 100 stearate, 1.5-3.5% cetyl alcohol, 0.5-1.5% stearyl alcohol, 0.5-1.5% theobroma cacao seed butter, 0.3-0.7% dimethoconol meadowfomate, 0.5-1.5% paraffinum liquidum, 0.5-2.5% sodium chloride PCA, 1-3% glycerin, 0.5-2.5% urea, 0.02-0.06% tetra sodium EDTA, 0.1-0.5% citric acid, 0.3-0.7% panthanol, 0.5-2.5% hydrolyzed corn protein, 0.5-1.5% hydrolyzed oat protein, 0.3-0.7% hydrolyzed soy protein, 0.5-1.5% sorbic acid, 0.1-0.3% methylisothiazolinone; 1.5-3.5% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia), 0.1-0.3% fragrance and a third solution comprising 82-86% water, 2-4% cetrimonium bromide, 0.5-2.5% glyceryl stearate and PEG 100 stearate, 1.5-3.5% cetyl alcohol, 1.5-3.5% stearyl alcohol, 0.5-1.5% glycerin, 0.3-0.7% tritcum vulgare (wheat) germ oil, 0.5-1.5% hydrolyzed corn protein, 0.3-0.7% hydrolyzed wool protein, 0.1-0.3% hydrolyzed collagen protein, 0.5-1.5% citric acid, 0.01-0.05% disodium EDTA, 0.03-0.07% methylisothiazzolinone, 0.05-1.5% sorbic acid 1-3% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia) and 0.1-0.3% fragrance and 0.1-0.3% PABA.

2. A method for straightening or curling hair comprising the steps of shampooing the hair;

drying the hair thoroughly;

shaking a bottle of a first solution to remove any precipitates, said first solution comprising 75-80% water, 4-6% PEG-12, 2-5% hydrolyzed corn protein, 2-5% hydrolyzed soy protein, 2-5% urea, 0.5-2.5% polysorbate 20, 0.10-0.20% methylparaben, 0.02-0.06% propylparaben, and 0.5-1.5% phenoxyethanol 3-7% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia) and 0.5-1.5% fragrance;

spraying said first solution on the hair;

providing sufficient time for said first solution to soak into the hair;

applying to the hair soaked with said first solution a hot iron set a temperature between 400 and 450 degrees Fahrenheit;

with said hot iron, straighten the hair using tension and a comb between five and ten times as dictated by the type of hair;

spraying a second solution on the hair, said second solution comprising 74-77% water, 3-7% stearylkonium chloride, 2-5% glyceryl stearate and PEG 100 stearate, 1.5-3.5% cetyl alcohol, 0.5-1.5% stearyl alcohol, 0.5-1.5% theobroma cacao seed butter, 0.3-0.7% dimethoconol meadowfomate, 0.5-1.5% paraffinum liquidum, 0.5-2.5% sodium chloride PCA, 1-3% glycerin, 0.5-2.5% urea, 0.02-0.06% tetra sodium EDTA, 0.1-0.5% citric acid, 0.3-0.7% panthanol, 0.5-2.5% hydrolyzed corn protein, 0.5-1.5% hydrolyzed oat protein, 0.3-0.7% hydrolyzed soy protein, 0.5-1.5% sorbic acid, 0.1-0.3% methylisothiazolinone 1.5-3.5% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia) and 0.1-0.3% fragrance;

straighten the hair four times with a flat iron with a comb and tension, said flat iron set at a temperature between 400 and 450 degrees Fahrenheit;

spray on the hair a third solution, said third solution comprising 82-86% water, 2-4% cetrimonium bromide, 0.5-2.5% glyceryl stearate and PEG 100 stearate, 1.5-3.5% cetyl alcohol, 1.5-3.5% stearyl alcohol, 0.5-1.5% glycerin, 0.3-0.7% tritcum vulgare (wheat) germ oil, 0.5-1.5% hydrolyzed corn protein, 0.3-0.7% hydrolyzed wool protein, 0.1-0.3% hydrolyzed collagen protein, 0.5-1.5% citric acid, 0.01-0.05% disodium EDTA, 0.03-0.07% methylisothiazzolinone, 0.05-1.5% sorbic acid 1-3% of a combination of extracts of Gingko Biloba, Matricaria (Chamomilla Recuite), Orange Peel (Citrus Aurantinum Dulcis), Althea Officinialis, Yarrow (Achillea Millefolium), Fennel (Foeniciulum Vulgare) and Licorice (Glycyrrhiz Glabia), 0.1-0.3% fragrance and 0.1-0.3% PABA;

straighten the hair four times with a flat iron with a comb and tension, said flat iron set at a temperature between 400 and 450 degrees Fahrenheit;

let hair cool for 30 minutes;

rinse with water;

apply said third solution;

rinse with water;

style as desired.

* * * * *